(12) United States Patent
Ross et al.

(10) Patent No.: US 6,360,588 B1
(45) Date of Patent: Mar. 26, 2002

(54) MATERIALS AND METHODS FOR THE ANALYSIS OF SUBSTANCES PASSING THROUGH A MEMBRANE

(76) Inventors: Edward Allan Ross, 8917 SW. 42nd Pl., Gainesville, FL (US) 32608; Ian R. Tebbett, 2125 SW. 83rd Ct., Gainesville, FL (US) 32607; Charles J. Schmidt, 2200 NW. 11th Ave., Gainesville, FL (US) 32605; Timothy Patrick Griffin, 405 4th Ave., Melbourne Beach, FL (US) 32951; Margaret Wheland Couch, 3524 NW. 51st. Ave., Gainesville, FL (US) 32605

( * ) Notice: Subject to any disclaimer, the term of this patent is extended or adjusted under 35 U.S.C. 154(b) by 0 days.

(21) Appl. No.: 09/448,634

(22) Filed: Nov. 24, 1999

Related U.S. Application Data (60) Provisional application No. 60/141,376, filed on Jun. 28, 1999, and provisional application No. 60/110,119, filed on Oct. 27, 1998.

(51) Int. Cl.⁷ .......................... G01N 15/08; G01N 13/04
(52) U.S. Cl. ............................................ 73/38; 73/64.47
(58) Field of Search .................. 73/38, 64.47; 422/101, 422/102

(56) References Cited

U.S. PATENT DOCUMENTS

| | | | | |
|---|---|---|---|---|
| 3,604,246 A | * | 9/1971 | Toren ............................ | 73/38 |
| 4,468,951 A | * | 9/1984 | Garcia et al. ................... | 73/38 |
| 4,852,389 A | * | 8/1989 | Mayer et al. ................... | 73/38 |
| 4,863,696 A | * | 9/1989 | Saydek et al. ............... | 422/101 |
| 5,490,415 A | * | 2/1996 | Mak et al. .................. | 73/64.47 |
| 5,659,130 A | * | 8/1997 | Chung et al. ............... | 73/64.47 |
| 5,738,826 A | * | 4/1998 | Lloyd .......................... | 422/102 |

OTHER PUBLICATIONS

ASTM D 3985 –81.*

* cited by examiner

Primary Examiner—Hezron Williams
Assistant Examiner—Jay Politzer
(74) Attorney, Agent, or Firm—Saliwanchik, Lloyd & Saliwanchik (57) ABSTRACT

The subject invention pertains to the efficient and accurate detection and analysis of materials passing through a membrane. In a specific example the transport of materials through skin is analyzed. The subject method can allow accurate, precise, and specific real time measurements of compounds crossing a membrane. Accordingly, the subject method can save time in product development of pharmaceuticals, cosmetics, and protective clothing products, and can also reduce the need for animal and human testing.

21 Claims, 13 Drawing Sheets

MATERIALS AND METHODS FOR THE ANALYSIS OF SUBSTANCES PASSING THROUGH A MEMBRANE

CROSS REFERENCE TO A RELATED APPLICATION

This application claims priority from provisional applications U.S. Ser. No. 60/110,119, filed Nov. 27, 1998 and U.S. Ser. No. 60/141,376, filed Jun. 28, 1999.

BACKGROUND OF THE INVENTION

The subject invention relates to the study of the transport of substances through barriers or membranes. In a specific example, the materials and methods of the subject invention can be used to study the transport of substances through skin.

Prior techniques for studying the transport properties of various substances through skin are expensive, labor intensive, and fail to yield time-dependent transport data. One such technique includes exposing mice to a substance under study and then analyzing the urine, blood, or actual skin tissue of the mice. In contrast, the subject technology is less expensive, less labor intensive, and yields time-dependent transport data.

At present, both in vivo and in vitro animal studies are employed to evaluate transdermal penetration characteristics of chemicals. The in vivo studies involve restraining an animal so that the material can be placed on it and insure that the substance will not be licked off or evaporate. The animal must then be housed, and urine or other biological samples collected. Typically, the animal is killed and the distribution of the applied material determined by, for example, extraction of animal parts. In vitro studies are somewhat simpler. The animal's skin is removed from the animal and placed in a diffusion cell where it is suspended on top of a liquid, one or more chemicals are placed on the skin and subsequently diffuses through the skin into the liquid. This liquid is then analyzed for the applied compound(s).

In conventional membrane introduction mass spectrometry (MIMS), samples are introduced into a mass spectrometer through a probe having a membrane across its tip. The probe is then inserted into the ion source portion of the mass spectrometer. A mesh support can be placed on the mass spectrometer side of the membrane to hold the membrane in place when the probe is inserted into the ion source, which is under vacuum. This membrane is typically made of silicone, and serves to control the introduction of the substance under study into a mass spectrometer. Typically, the focus is not on the membrane, or the interaction of the substance. Rather, MIMS is generally concerned with determining the constituents of a substance in a liquid form. In order to volatilize the sample and mobile phase, the source is usually run at temperatures exceeding 200° C. Mobile phase is pumped over the membrane allowing the analyte to diffuse through the membrane into the MS source. Once in the MS source, the analyte breaks apart to give characteristic fragments, identifying the constituents of the analyte. A major portion of the mobile phase that passes through the membrane is removed by the vacuum pumping system. In addition, the mass spectrometer can be adjusted so that it will not "see" the remaining mobile phase ions. This technique is adequate when one wishes to identify components in a liquid. Both the vacuum and the temperature of the source can, however, drastically alter the permeability characteristics of a membrane.

Accordingly, a method and device which would allow diffusion across the membrane to occur at ambient conditions would be beneficial.

BRIEF SUMMARY OF THE INVENTION

The subject invention provides unique instrumentation and methods useful in the quantitative and qualitative evaluation of the transport of compounds across a membrane. In a specific embodiment, the subject invention pertains to the use of a membrane atmospheric pressure interface (MAPI) to investigate the penetration/permeation and transport of substances across materials. In a preferred embodiment, the movement of materials through skin are analyzed in a time-dependent manner with great accuracy.

In contrast to membrane introduction mass spectrometry (MIMS), MAPI can allow one to expose a first side of fabric, skin membrane, or other material to a substance and study the amount per time of the substance which exits the other side of the skin, fabric, or other material. Analysis of this time-dependent data can allow one to determine the transport properties of the known substance through that membrane. A further aspect of the subject invention is the ability to determine if an analyte is degraded or otherwise modified as it interacts with, or passes through the membrane.

The subject technology can utilize human, animal, artificial, and/or synthetic skin, and is particularly advantageous for kinetics studies and synergistic effects studies involving the dependence of the transport properties of one substance on the presence of another substance. Similarly, the subject technology can be used to evaluate the permeation rate, breakthrough time and normalized breakthrough time of substance(s) through materials used for chemical protective clothing.

Although mass spectrometry is specifically exemplified herein as a preferred means for detecting analytes passing through the membrane, other forms of detection including, for example, gas chromatography, high performance liquid chromatography, and biological assay, can all be used for detecting compounds which have passed through the skin membrane.

BRIEF DESCRIPTION OF THE DRAWINGS

FIG. 6 shows a MAPI apparatus which utilizes a pinch lamp to hold the donor compartment and receptor compartment together with the membrane under study clamped between.

DETAILED DISCLOSURE OF THE INVENTION

The subject invention provides materials and methods useful in analyzing the transport of substances through barriers or membranes. In a specific example, the materials and methods of the subject invention can be used to study the transport of substances through skin. The subject method can allow accurate, precise, and specific real time measurements of compounds crossing a membrane. Accordingly, the subject method can save time in product development of pharmaceuticals, cosmetics, and protective clothing products, and can also reduce the need for animal and human testing.

In accordance with the methods of the subject invention, a composition can be applied to one side of a membrane, for example skin. The identity and quantity of compounds passing through the membrane and exiting the other side of the membrane can then be determined in a time dependent manner. The skilled artisan having the benefit of the teachings provided herein could utilize a variety of detection means including, but not limited to, mass spectrometry, high performance liquid chromatography, gas chromatography, liquid chromatography, FID, electrochemical analysis, photodiode array, PDA, UV/VD, HAL, atomic absorption (AA), inductive coupled plasma (ICP), ICPMS, fluorescence, and biological assays. In a specific embodiment, the subject diffusion apparatus can be used in tandem with liquid chromatography/mass spectrometry/mass spectrometry (LC/MS/MS).

Figure 5:
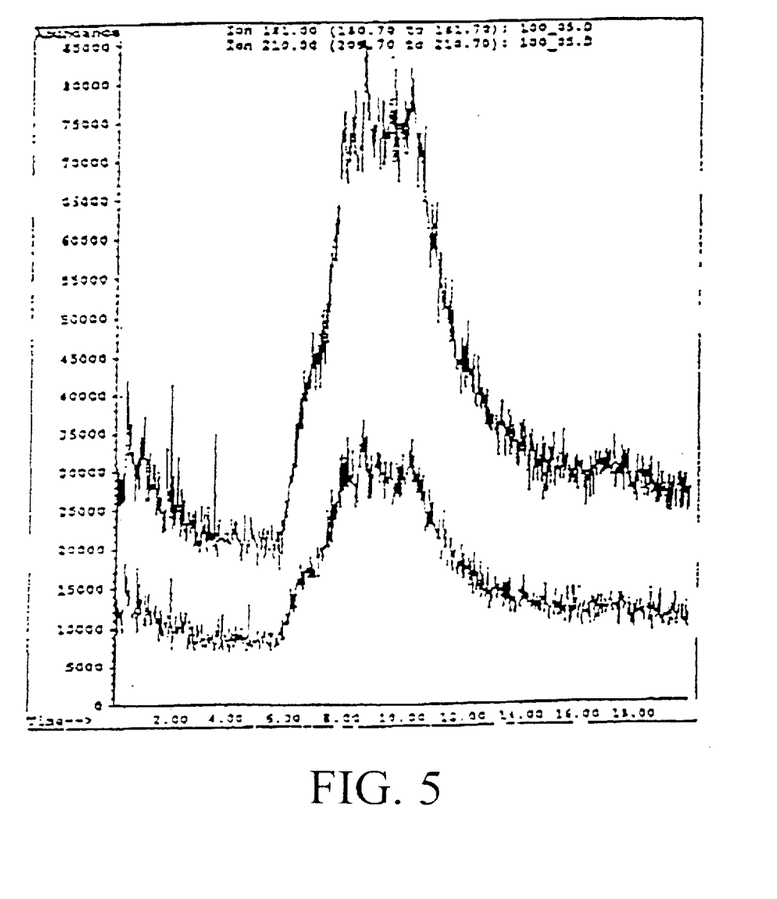
FIG. 5 shows an ion chromatogram of aromatic hydrocarbon using a standard MIMS probe as a MAPI interface with a skin membrane, in accordance with the subject invention.

In a specific embodiment, skin from hairless mice has been used in accordance with the subject invention to demonstrate that skin can act as a semi-permeable membrane for a MIMS probe. Specifically, when an aliquot of diluted aromatic hydrocarbon is placed in the sample chamber, extracted ion chromatograms based on characteristic ions showed that the compound slowly diffused through the skin. FIG. 5 shows an ion chromatogram of aromatic hydrocarbon using a standard MIMS probe as a MAPI interface with a skin membrane. Other detection means can also be used to detect the substances which have passed through the skin.

The techniques of the subject invention are advantageous because they are not as complicated as methods now used in the animal studies for the evaluation of transdermal penetration, and can provide studies of drug delivery in much less time. The methods of the subject invention can be employed as rapid analytical screening techniques to investigate and evaluate the penetration of chemicals through the skin or another biological membrane. Additionally, the MAPI using artificial skin as a membrane may reduce, or totally eliminate, the use of animals.

The subject technology can utilize human, animal, artificial, and/or synthetic skin. In a preferred embodiment, the probe of the subject invention may be specifically adapted to maintain the integrity and viability of the skin membrane. For example, the membrane may be bathed in a fluid comprising oxygen, saline, and/or nutrients so as to best retain the physiological properties of the skin. By maintaining the physiological properties of the skin it is possible to best simulate the actual conditions of transport across skin.

Drugs applied to human, animal or synthetic skin can be monitored to determine their absorption kinetics. The subject method can be utilized with drugs delivered, for example, via creams, ointments, sprays and patches. In addition to monitoring a drug of interest, the subject technique can allow any excipients and carriers to be monitored. With respect to any excipients and/or carriers, it may be beneficial to minimize absorption. Information concerning rate of absorption, time to steady state, peak concentration at steady state, rate of elimination, and duration of action can be readily determined.

The subject method and device can enable real time measurements to be made to evaluate the effects of changing the formulation of the pharmaceutical preparation on drug absorption e.g. the effect of any interactions with other drugs, excipients and carriers. The fact that the diffusion apparatus is in line with the analytical device allows real time measurements, reduces operator influences, and can therefore save time in product development. The subject invention can allow the study of the pharmakinetics of the substances under study, thus allowing the generation of accurate data regarding the transients portions of the diffusion curves. Decisions concerning the optimization of the physical chemical characteristics of the drug/prodrug, choice of excipients, carriers and adhesives can be made much more rapidly than with traditional transdermal absorption measurement techniques. A library of kinetic data associated with transdermal formulations can be utilized to quickly identify candidate carrier systems for different classes of drugs.

The subject method can allow the ready comparison of multiple formulations of the same product, e.g., generics, and quality control assays of different batches of the product. The compatibility of the diffusion apparatus with an array of detection devices makes it applicable to the analysis for a wide range of compounds including small drug molecules as well as high molecular weight compounds such as proteins, peptides and DNA fragments.

Diffusion apparatus in accordance with the subject invention can be used such that components of, for example, cosmetic preparations and insect repellants, remain on the skin surface and are not absorbed into the systemic circulation. The subject apparatus can be used to assess the transdermal absorption of industrial hazards including chemicals, solvents, carbonless copy paper and environmental toxicants such as pesticides, polyaromatic hydrocarbons and polychlorinated biphenyls (PCBs).

The subject apparatus can be used to study any membrane and, for example, can enable the determination of the effectiveness of protective clothing, including gloves, as a barrier to given chemicals, biologicals and toxicants. This can allow selection of optimal protective clothing, for example, with respect to medical and laboratory protective clothing, and clothing for emergency personnel including firefighters, who may be exposed to hazards associated with chemical fires.

A further advantage of the subject invention is that it possible to evaluate the possible transformation of compounds as they pass through the skin by detecting what exits the skin after diffusion. Such transformation can include, for example, the formation of complexes, breakdown products, metabolites and the like. The methods of the subject invention make it possible to detect such transformants in a time-dependent manner.

A further advantage of the subject invention is that it can isolate the skin (compared to, for example, in vivo mouse studies) such that biological and physiological factors unrelated to transdermal transport can be eliminated.

In a specific embodiment, the materials and methods of the subject invention can be used to readily and accurately assess the ability of various compounds to inhibit or promote movement through skin. Such compounds can be added to a formulation and evaluated as to how they affect transport of a second compound. The affect of chemical modification on the transport properties of a particular molecule can also be analyzed.

The methods of the subject invention can also be used to evaluate the ability of lotions or other barrier compositions to prevent or inhibit the transport of toxins through the skin.

The subject invention is particularly advantageous for kinetics studies and synergistic effects studies involving the dependence of the transport properties of one substance on the presence of another substance. As an example, it is often important to know how the presence of one substance, such as cosmetics, affects the absorption and diffusion of another substance, such a potentially toxic material, by and through the skin.

In addition to the study of drug delivery, this technology can be used in the study of the absorption of environmental contaminants, for example gasoline absorption through the skin. This technology can also be used to evaluate materials in chemical protective clothing that is used by, for example, emergency personnel. These materials are supposed to protect the wearer against hazardous substances such as insecticides, industrial chemicals and chemical warfare agents. It can identify components in mixtures and compare the kinetics of penetration by a single compound with its kinetics when in a mixture.

Following are examples which illustrate procedures for practicing the invention. These examples should not be construed as limiting.

EXAMPLE 1

Figure 1:
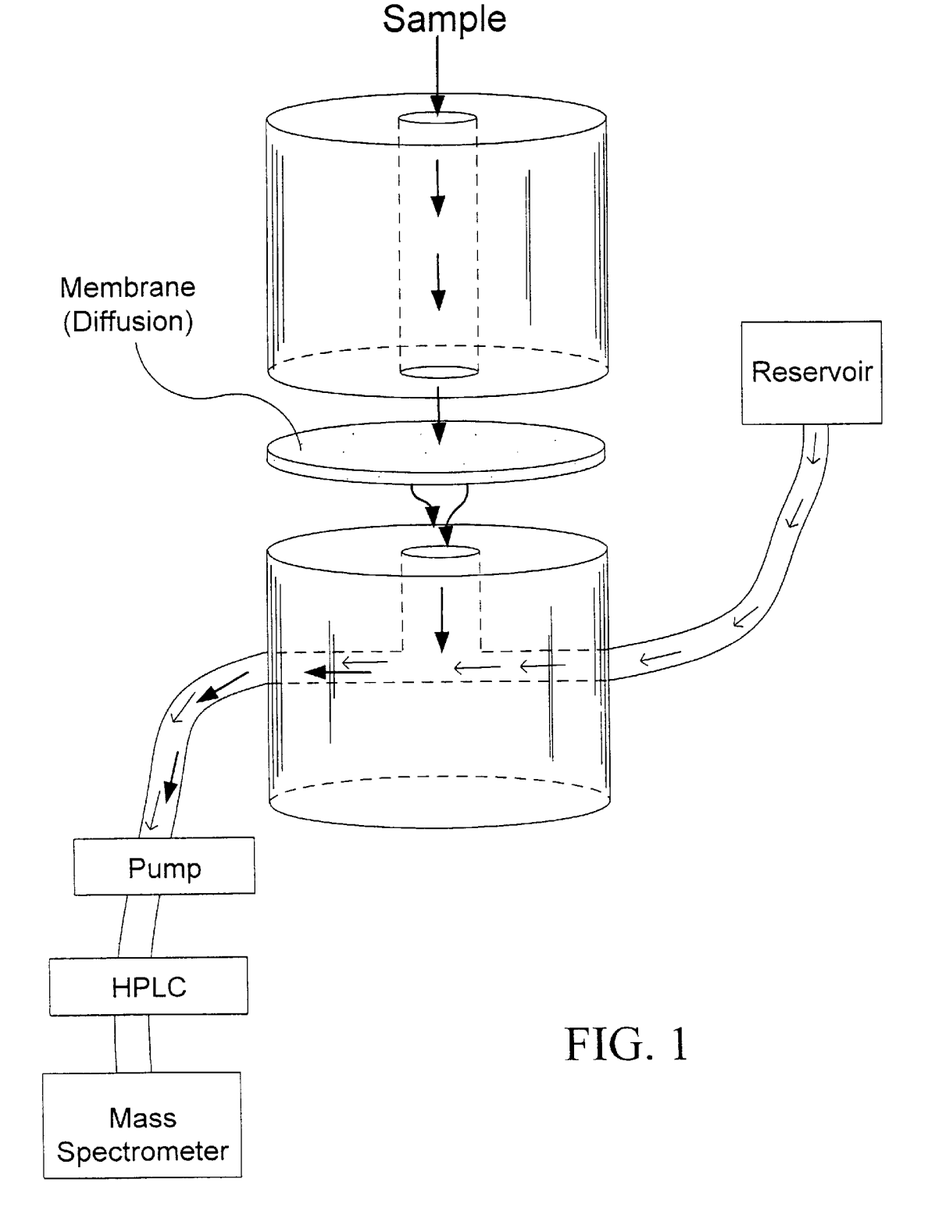
FIG. 1 shows the construction and principal of operation of a MAPI in accordance with the subject invention, which can be used to introduce samples into a mass spectrometer by applying sample to one side of a membrane held by the interface.

Referring to FIG. 1, a MAPI is shown which allows a sample to be applied to one side of a membrane and a carrier fluid from a reservoir to pass by the other side of the membrane to carry any sample diffusing through the membrane to be detected. Preferably, the sample is at atmospheric pressure, but can also be at other desired pressures. In the embodiment shown in FIG. 1, the pump is located after the membrane to reduce the pressure exerted on the membrane and the corresponding risk of rupture. The time artifacts of the pump can be monitored and removed from the detection data. A high pressure liquid chromatology (HPLC) machine can act as a UV/VD detector which looks at the absorbance of the fluid flowing through. Finally, the fluid can then be injected into a mass spectrometer for further analysis.

EXAMPLE 2

Figure 2:
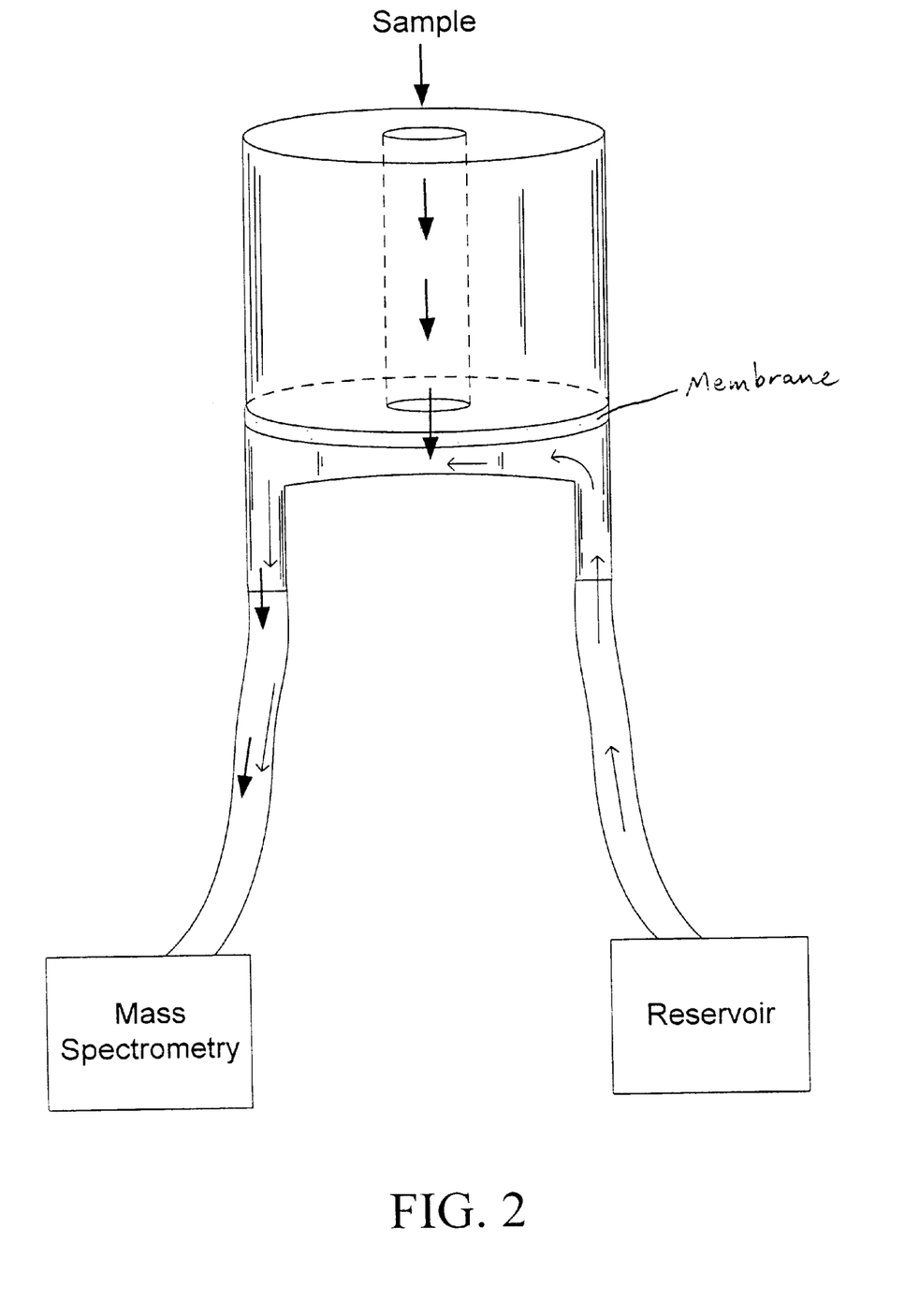
FIG. 2 shows a standard MIMS probe being utilized for MAPI, in accordance with the subject invention.
Figure 3:
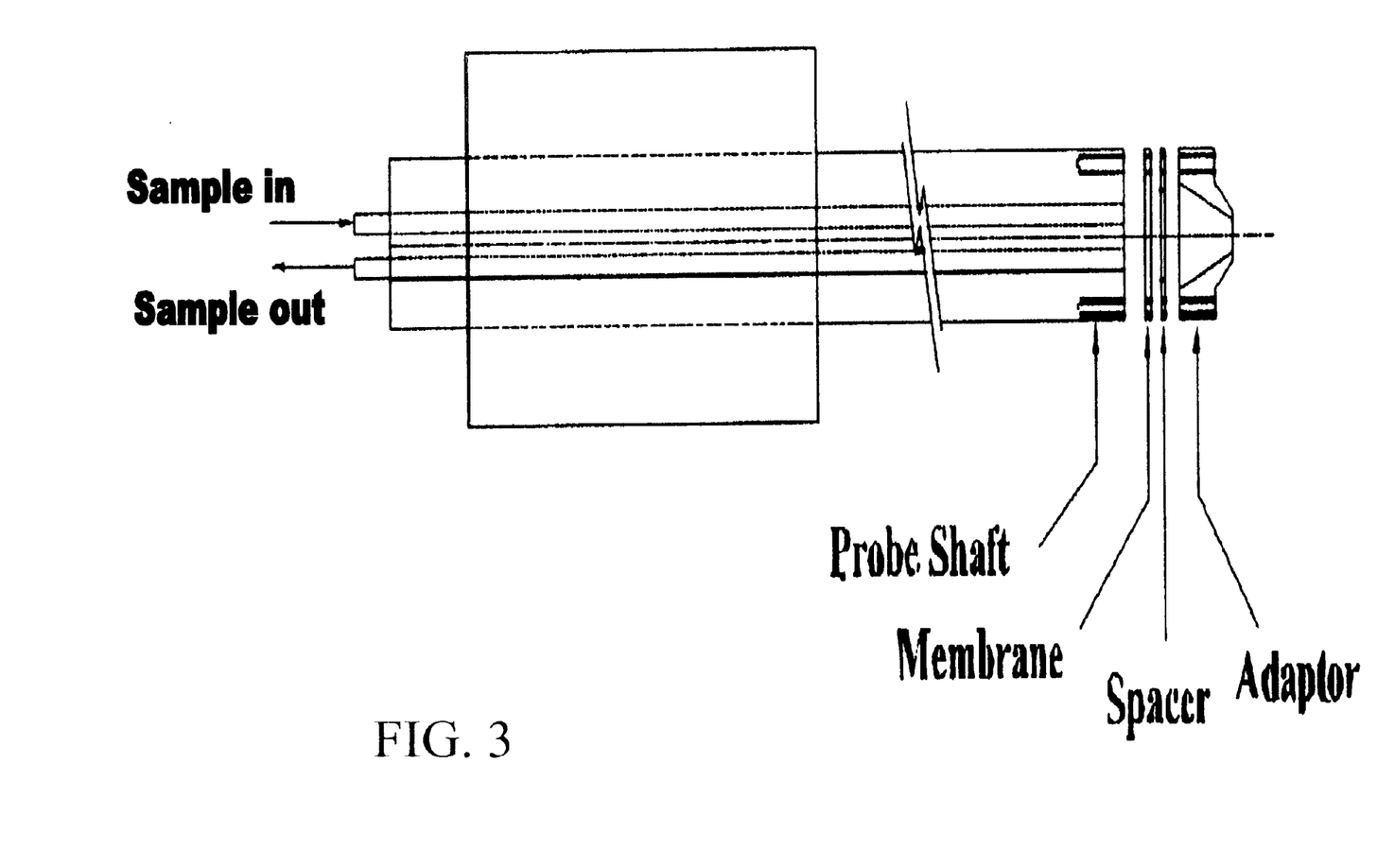
FIG. 3 shows a standard MIMS probe which can utilize a skin membrane for insertion into the ion source of a mass spectrometer.

A simple MAPI was made as described in FIG. 2. The MAPI in FIG. 2 utilizes a standard MIMS probe as shown in FIG. 3, wherein instead of the sample to be studied flowing in and out of the probe connections to diffuse through the membrane and enter the mass spectrometer, the sample is introduced on the other side of the membrane. A carrier fluid is then introduced into one of the probe's connections and carries any sample diffusing through the membrane out the other probe connection to be analyzed by, for example, a mass spectrometer. The MIMS probe was used with synthetic polymer membranes. The subject invention is unique and advantageous, because it utilizes animal skin or synthetic skins as the membrane for the MAPI. Skin from a hairless mouse has been shown to act as a semi-permeable membrane for the MAPI. Specifically, when an aliquot of diluted aromatic hydrocarbon was injected into mobile phase circulating through the MIMS probe, extracted ion chromatograms (using the characteristic ions) showed that the compound slowly diffused through the skin into the source. FIG. 5 shows an ion chromatogram of aromatic hydrocarbon using a standard MIMS probe as a MAPI interface with a skin membrane. A wide range of compounds can be detected by the method of the subject invention.

EXAMPLE 3

Figure 4:
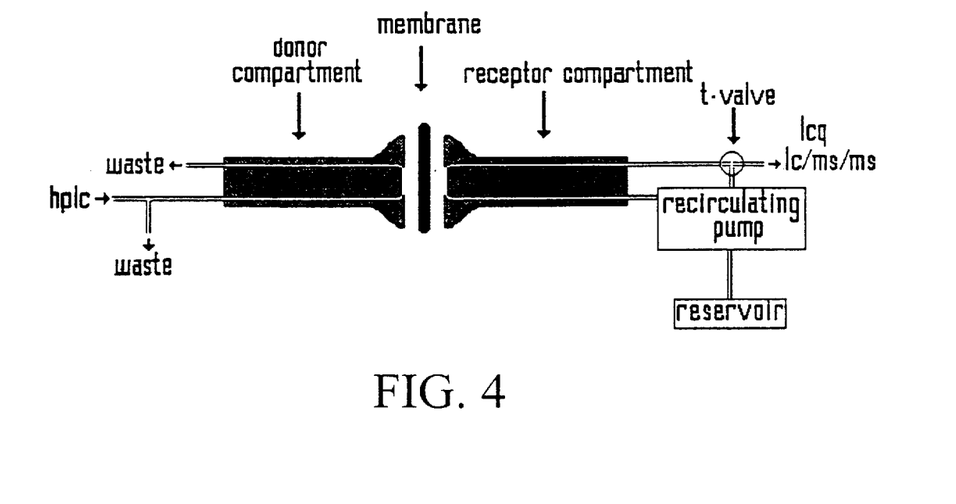
FIG. 4 shows a specific embodiment of a MAPI apparatus in accordance with the subject invention.

FIG. 4 illustrates another specific example of a MAPI in accordance with the subject invention.

EXAMPLE 4

Figure 6:
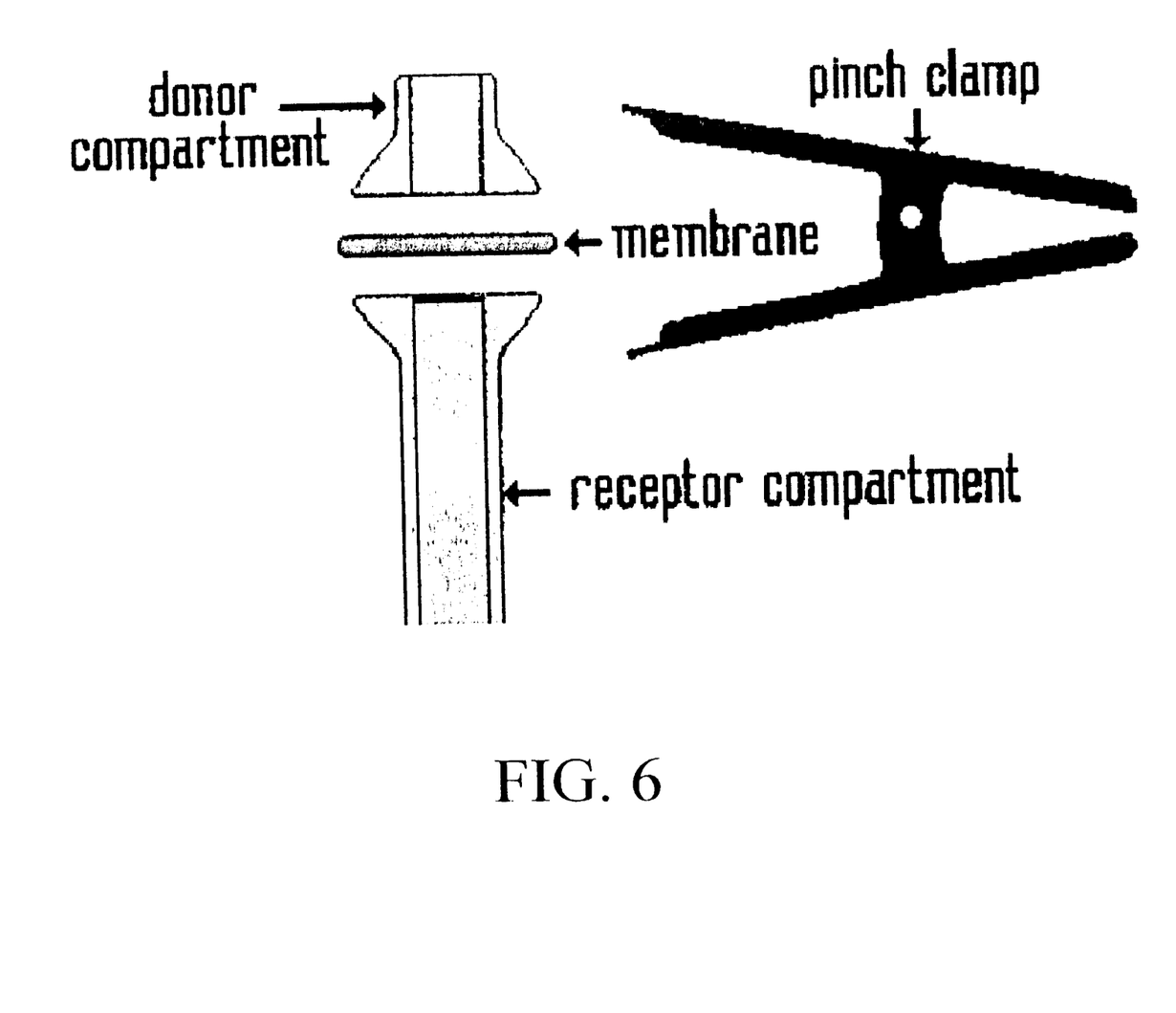

FIG. 6 illustrates another specific example of a MAPI in accordance with the subject invention. The donor compartment and the receptor compartment can be held together by a pinch clamp with the membrane under study in between. A patch can be placed on the membrane, for example on a skin membrane, to study the effects of the patch on diffusion of samples under study. Accordingly, the patch can also be held between the compartments by the pinch clamp. Alternatively, the patch can be attached to the membrane.

EXAMPLE 5

Figure 7A:
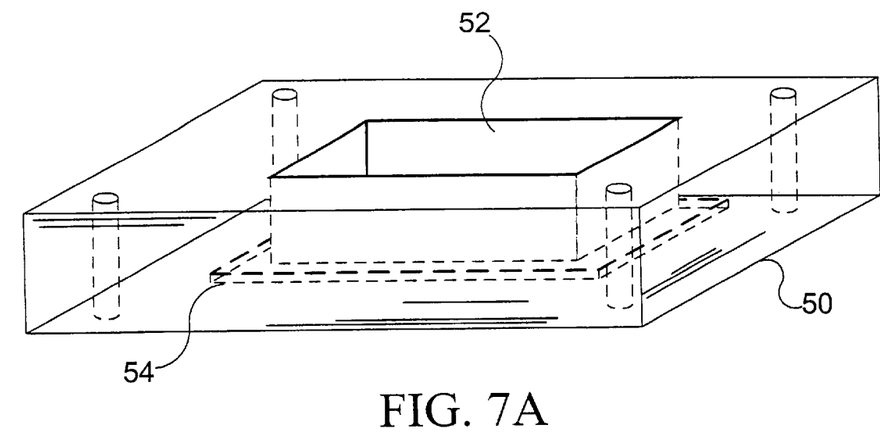
FIGS. 7A, 7B, and 7C show a specific embodiment of a device for holding a membrane under study.
Figure 7B:
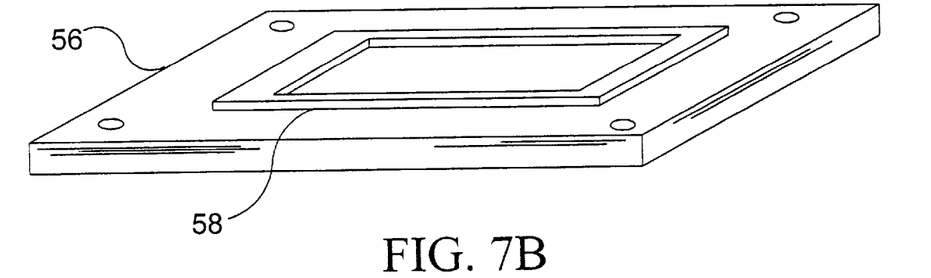
Figure 7C:
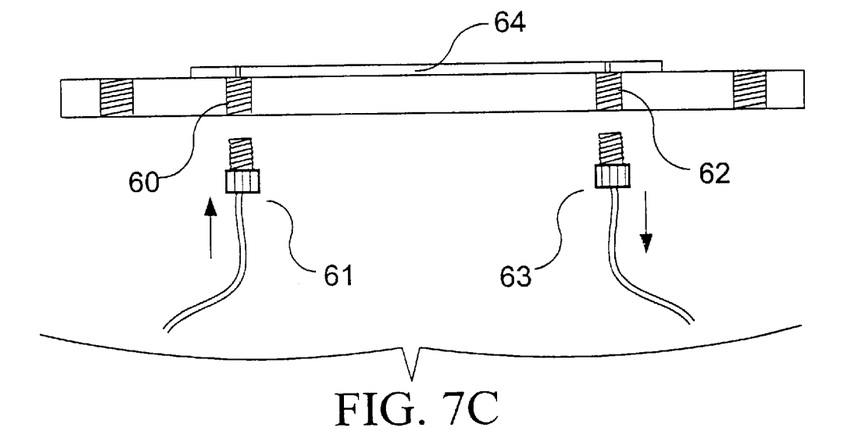

Referring to FIGS. 7A, 7B, and 7C, a specific embodiment of a device for holding a membrane under study is shown. Top portion 50 can have bore 52 therethrough from top to bottom which allows a substance under study to be placed in contact with a membrane under study. The bottom of top portion 50 can have a recessed portion 54 for receiving a membrane under study. Bottom plate 56 can have means for attaching securely to top portion 50 such as to hold a membrane under study securely in place. A spacer 58 can be used to hold a membrane in position between bottom plate 56 and top portion 50. Spacer 58 can also have a bore there through from top to bottom, preferably the same dimensions as bore 52 and more preferably positioned to be aligned with bore 52 once top portion 50 and bottom plate 56 are secured together. Accordingly, a membrane under study can be positioned on top of spacer 58, which can then be placed on bottom plate 56 such that when bottom plate 56 and top portion 50 are brought together, the membrane and spacer 58 are maneuvered into recessed portion 54. The bottom plate 56 and top portion 50 can then be secured together. Multiple spacers 58, having a variety of thicknesses can be available to accommodate membrane of various thicknesses. Spacer 58 can be made of, for example, Teflon.

A substance for which a transport or absorption characteristic is to be studied can then be put into bore 52 and in contact with a first side of the membrane. Referring to FIG. 7C, a side view of spacer 58 resting on top of bottom plate 56 shows a small volume 64 is created by the bore in spacer 58, between the membrane and the top of bottom plate 56. Access ports 60 and 62 can allow a carrier fluid to enter into volume 64 through input access port 60, flow through the volume 64, and exit the volume 64 through output access port 62. Carrier fluid conduits 61 and 63 can be used for such input and output of carrier fluid. The flow of the carrier fluid through volume 64 allows contact with a second side of the membrane such that the carrier fluid can carry any substances exiting the second side of the membrane a detection apparatus for analysis.

In a specific embodiment, bore 52 can be approximately 1 inch by 3 inch and 1 inch depth. This can add a sufficient amount of contact between the substance under study to allow the study of very slow diffusing substances such as those delivered by a patch. Other dimensions can be utilized for specific applications.

In operation, once the membrane and spacer are in place and the top portion 50 and bottom plate 56 are secured, a substance under study can be placed in contact with the first side of the membrane. Carrier fluid can be flowing through volume 64 and to a detection means. As the substance diffuses through the membrane and exits the second side of the membrane, it can be carried to the detection apparatus for analysis. In this way, an accurate time dependent curve can be generated as to the amounts of the substance under study exiting the second side of the membrane.

EXAMPLE 6

This example illustrates the results from diffusion of a variety of substances through polydimethylsiloxane membrane obtained from PILLAR SCIENTIFIC, ranging in thickness from 0.01 inches to 0.05 inches. A mass spectrometer was used as a detection apparatus with electrospray ionization utilized to ionize the sample for detection in the mass spectrometer.

Figure 8A:
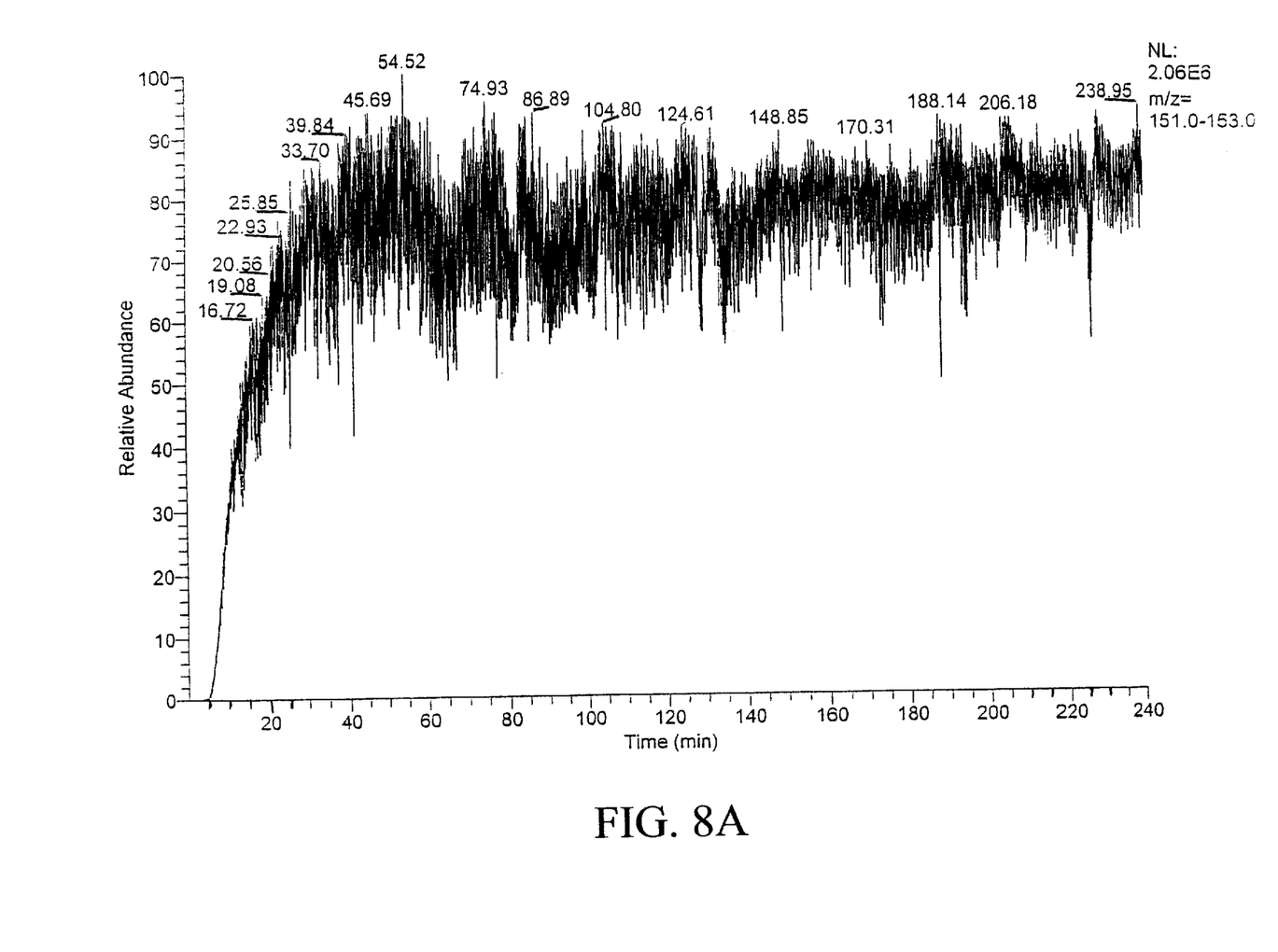
FIGS. 8A and 8B illustrate curves showing the relative abundance of methyl paraben exiting the second side of a polydimethylsiloxane membrane as a function of time and relative to other mass-to-charge ratio ions from 100 m/z to 300 m/z, respectively.
Figure 8B:
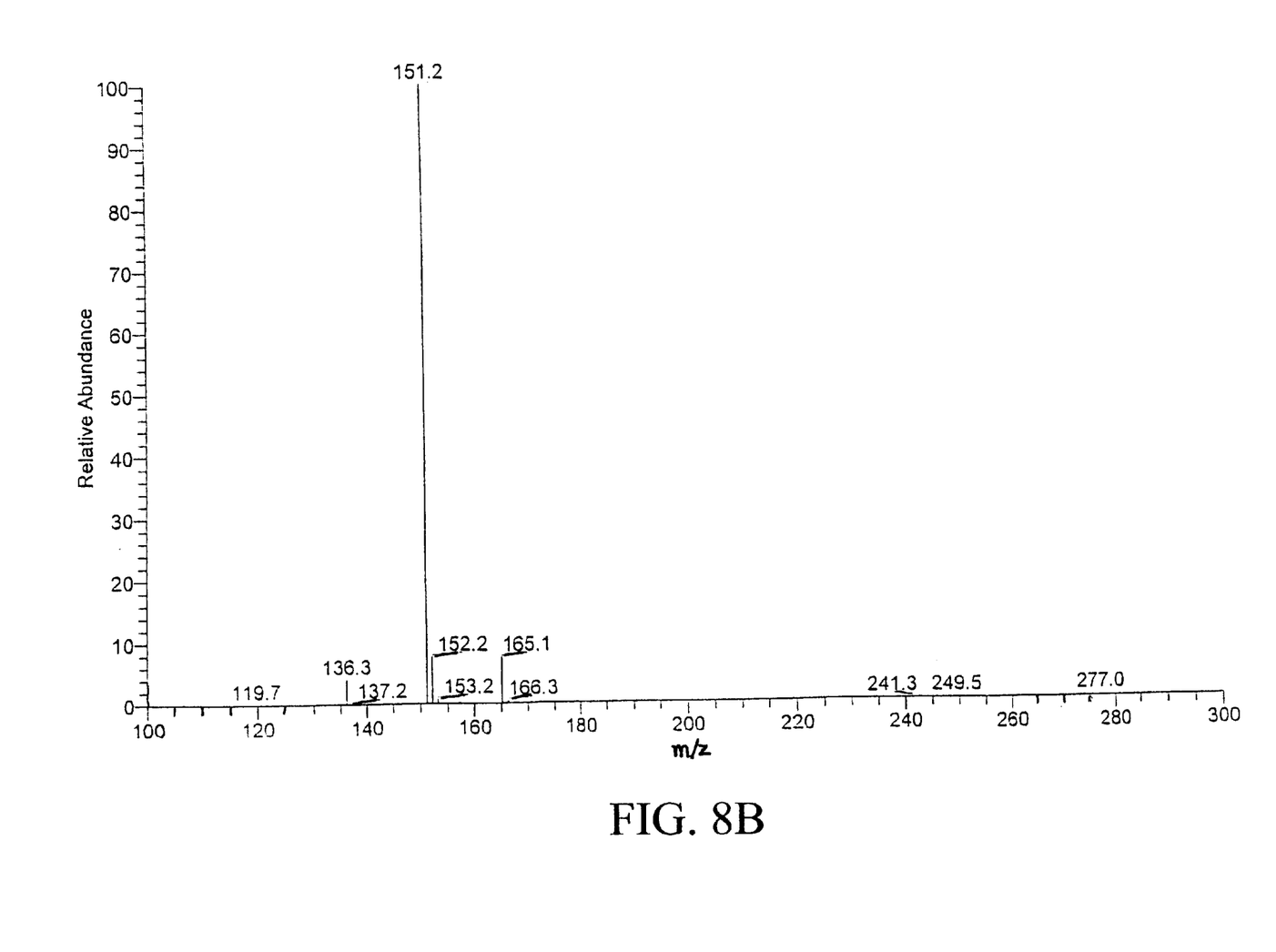

Referring to FIGS. 8A and 8B, the relative abundance of methyl paraben exiting the second side of the membrane after exposure to the first side is shown as a function of time and relative to other mass-to-charge ratio ions from 100 m/z to 300 m/z. It can be seen that a time-dependent curve can be achieved, showing the diffusion of methyl paraben through the polydimethylsiloxane membrane.

Figure 9A:
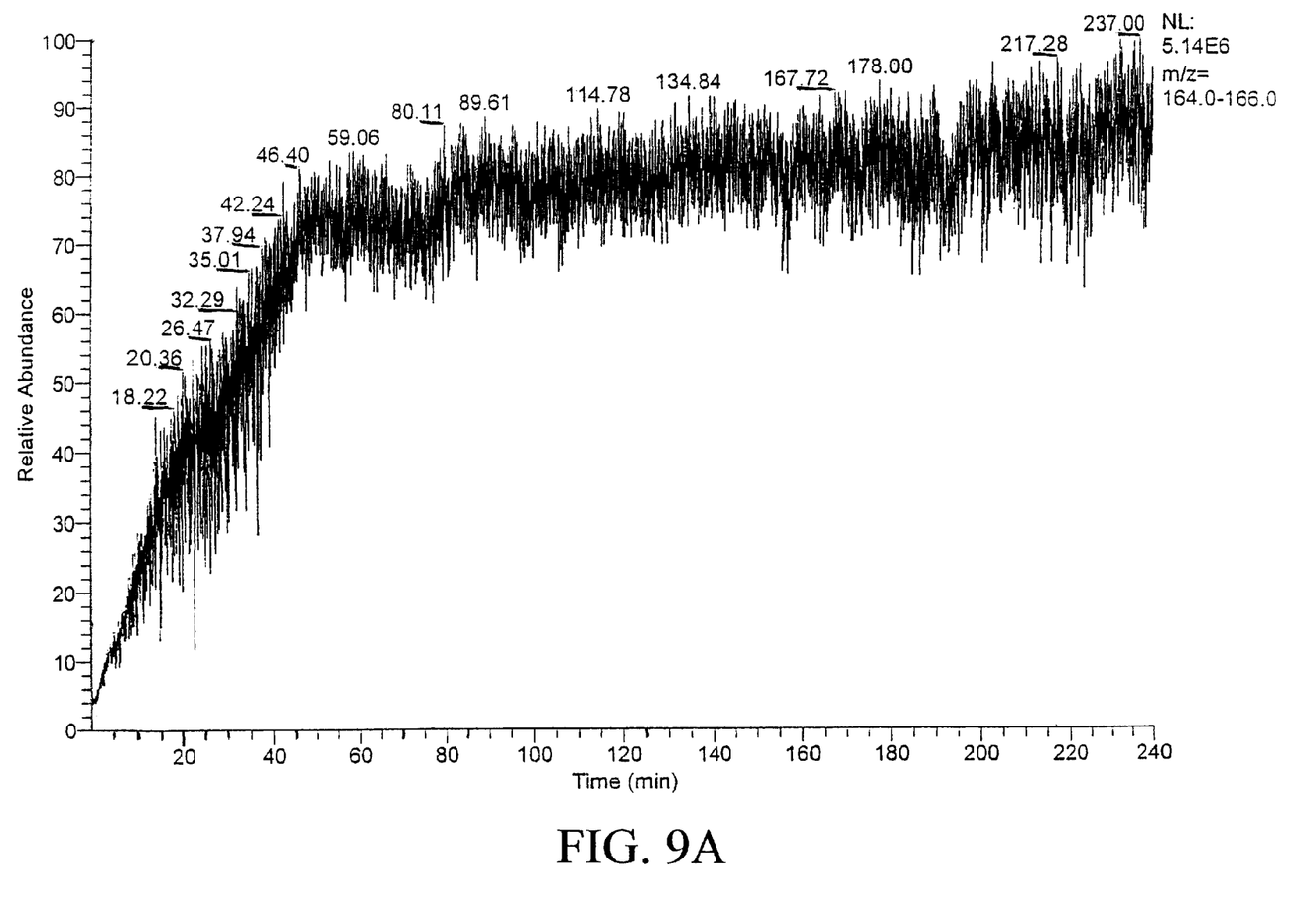
FIGS. 9A and 9B illustrate curves showing the relative abundance of ethyl paraben exiting the second side of a polydimethylsiloxane membrane as a function of time and relative to other mass-to-charge ratio ions from 100 m/z to 300 m/z, respectively.
Figure 9B:
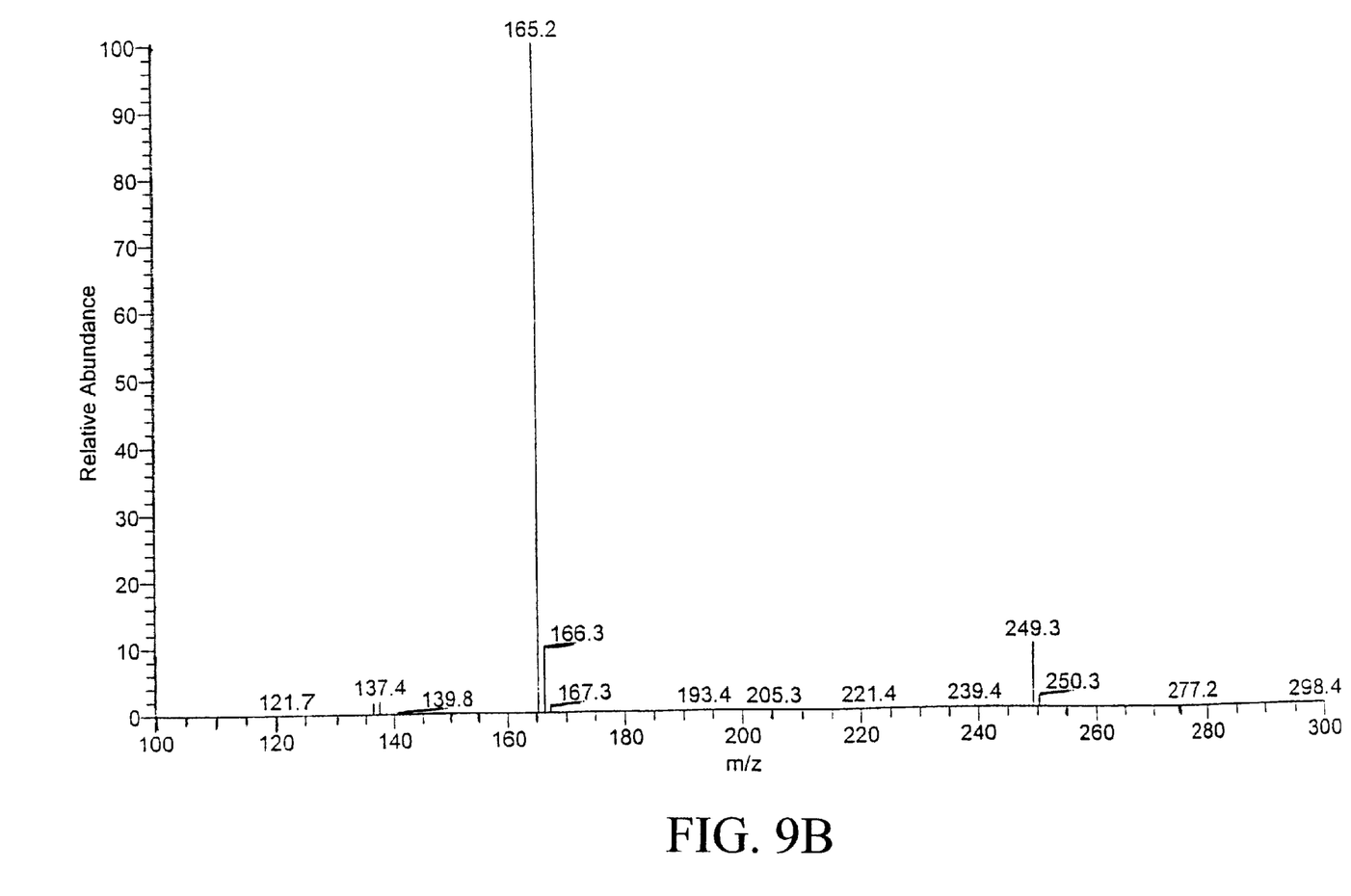

Referring to FIGS. 9A and 9B, the relative abundance of ethyl paraben exiting the second side of the membrane after exposure to the first side is shown as a function of time and relative to other mass-to-charge ratio ions from 100 m/z to 300 m/z. It can be seen that a time-dependent curve can be achieved, showing the diffusion of ethyl paraben through the polydimethylsiloxane membrane.

Figure 10A:
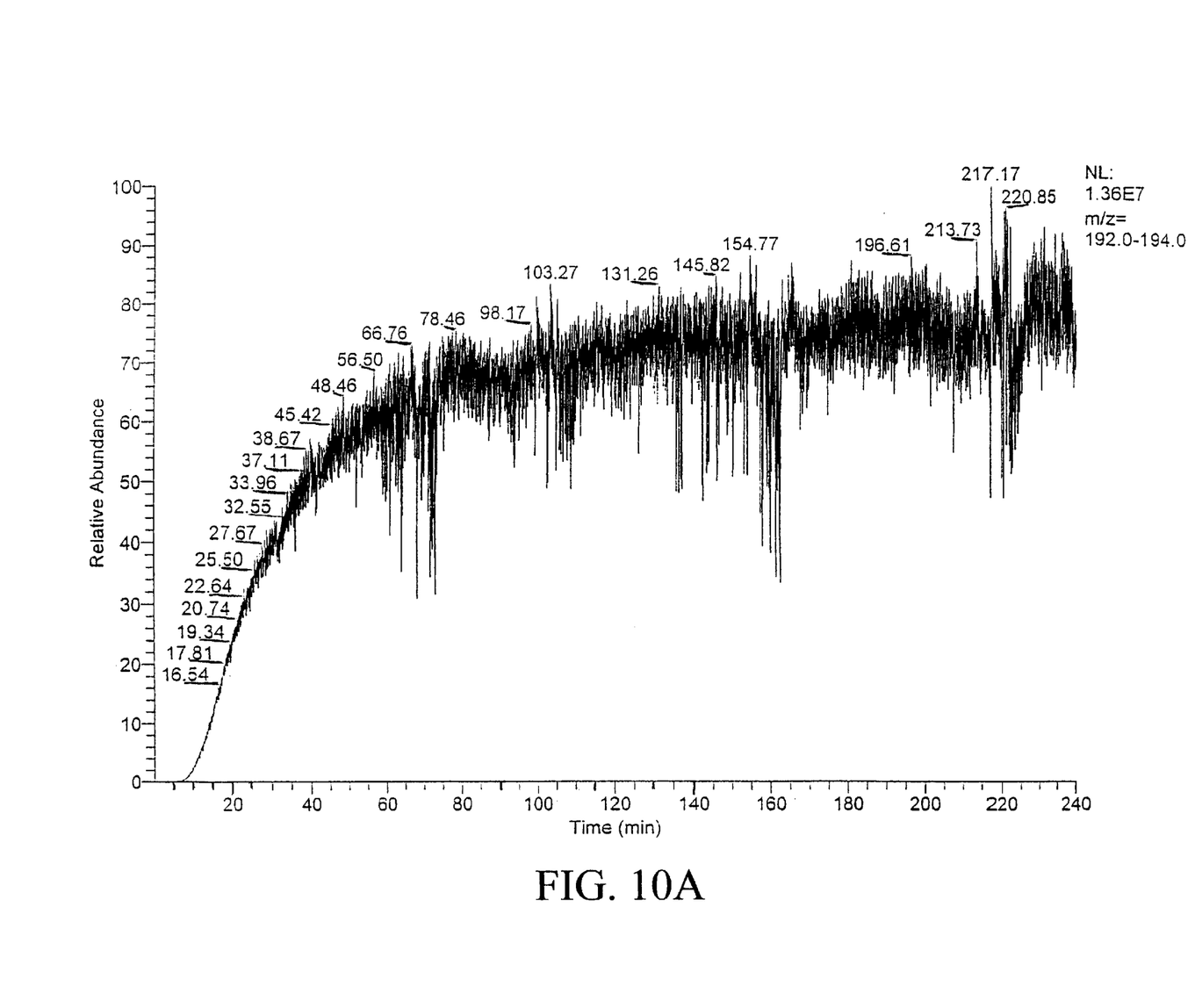
FIGS. 10A and 10B illustrate curves showing the relative abundance of n-butyl paraben exiting the second side of a polydimethylsiloxane membrane as a function of time and relative to other mass-to-charge ratio ions from 100 m/z to 300 m/z, respectively.
Figure 10B:
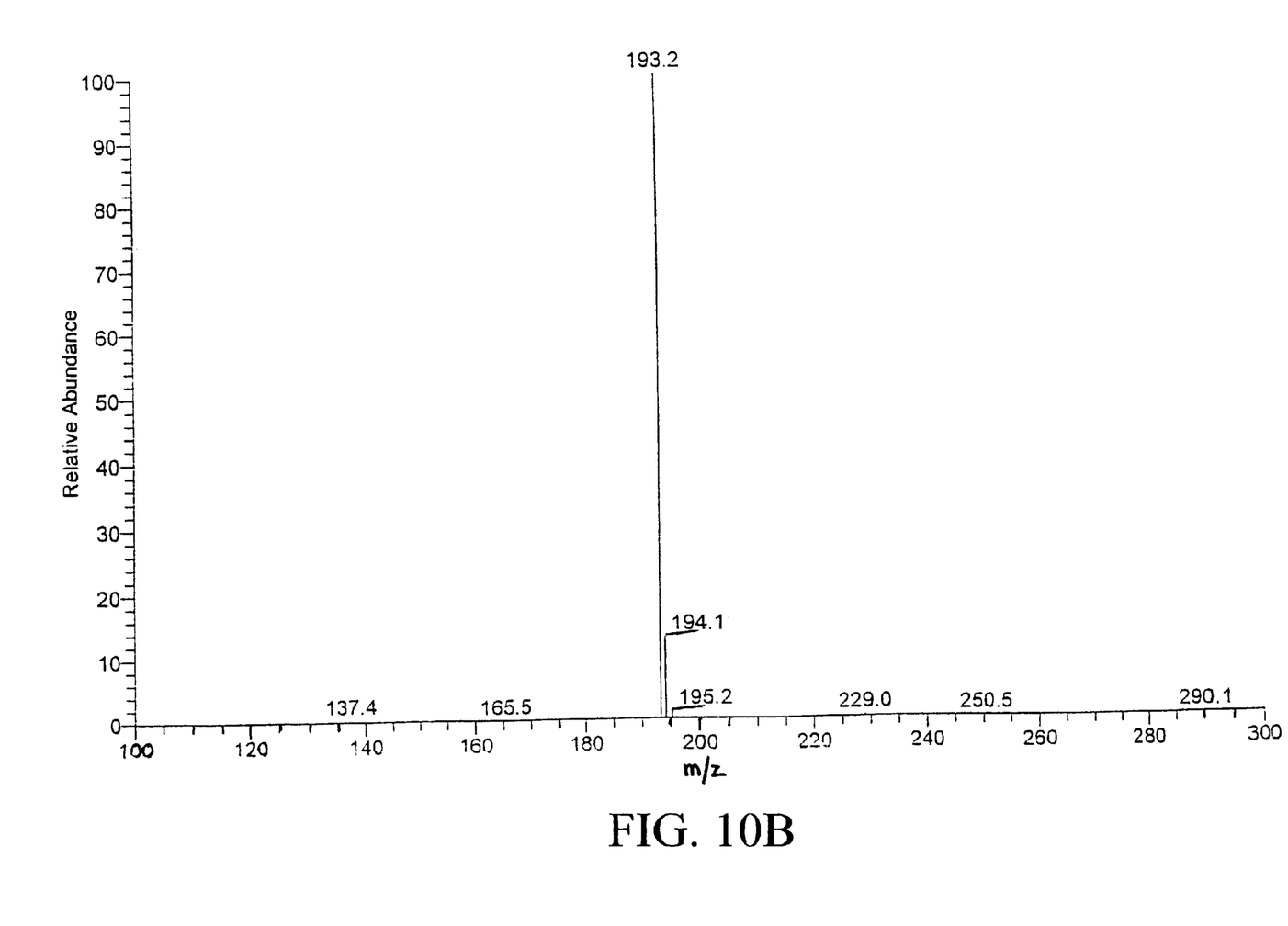

Referring to FIGS. 10A and 10B, the relative abundance of n-butyl paraben exiting the second side of the membrane after exposure to the first side is shown as a function of time and relative to the mass-to charge ratio ions from 100 m/z to 300 m/z. It can be seen that a time-dependent curve can be achieved, showing the diffusion of n-butyl paraben through the polydimethylsiloxane membrane.

Figure 11A:
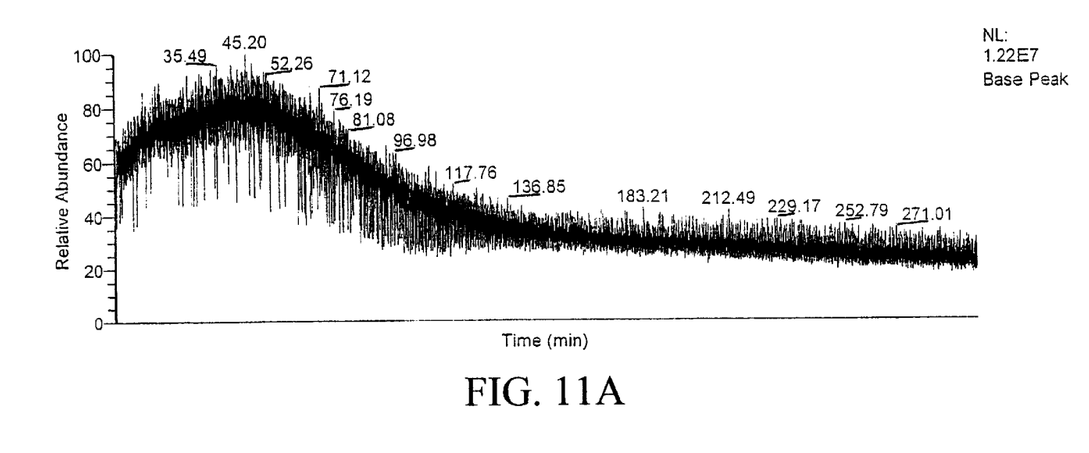
FIGS. 11A and 11B illustrate the relative abundance of total mixture, including solvent and clonidine, and the relative abundance of clonidine, respectively, exiting the second side of a polydimethylsiloxane membrane after placement of a clonidine patch on the first side of the membrane.
Figure 11B:
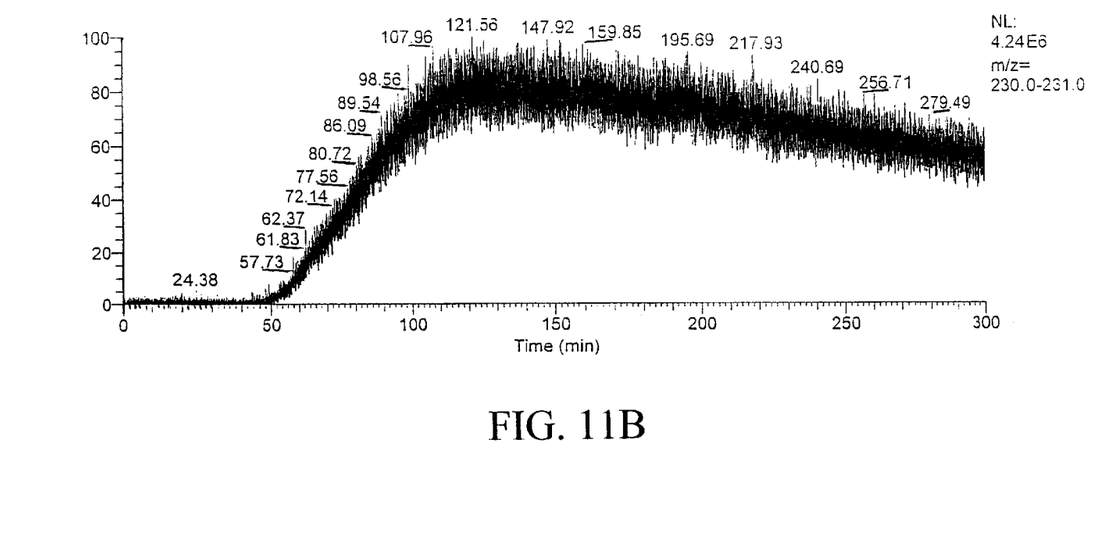

Referring to FIGS. 11A and 11B, the relative abundance of total mixture (FIG. 11A), including solvent and clonidine, and the relative abundance of clonidine (FIG. 11B), exiting the second side of the membrane after placement of a clonidine patch on the first side are shown as a function of time. It can be seen that a time-dependent curve can be achieved, showing the diffusion of the total mixture, and clonidine, respectfully, through the polydimethylsiloxane membrane. The ability to see the non-clonidine substances from the patch diffusing through the membrane and the clonidine diffusing through the membrane can be useful both to reduce the diffusion of potentially harmful substances and to optimize the dose of clonidine, or other helpful substances, through the membrane.

The diffusion curves illustrated in this example illustrate the type of valuable diffusion information which can be obtained with the techniques of the subject invention. Additional information can be obtained by implementing other aspects of the subject invention, including but not limited to, changing the thickness of the membrane; coating the membrane with one or more substances such as cosmetics, protective materials, lotions, and insect repellents; adding one or more additional substances to the sample containing the substance under study to be put in contact with the first side of the membrane; changing the surface area of the membrane; changing the pressure and or temperature to which the membrane is exposed; changing the carrier fluid; and changing the concentration of the substance under study to which the first side of the membrane is exposed.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of studying a transport characteristic of a substance through a barrier, comprising the following steps:
   exposing a first side of a barrier to a substance; and
   measuring an amount of said substance exiting a second side of said barrier, wherein said barrier is positioned in a MIMS probe, wherein the step of exposing the first side of the barrier to the substance is accomplished by placing said substance in a sample chamber of the MIMS probe, and wherein said MIMS probe is positioned in a mass spectrometer such that the step of measuring the amount of said substance exiting the second side of said barrier is accomplished when said substance exiting the second side of said barrier is detected by the mass spectrometer.

2. The method according to claim 1, wherein said barrier is selected from the group consisting of: human skin, animal skin, fabric, latex glove material, protective clothing, artificial skin, synthetic skin, and rubber.

3. The method according to claim 2, wherein said barrier is selected from the group consisting of: human skin, animal skin, synthetic skin, and artificial skin, wherein said barrier is bathed in a fluid comprising one or more of the group consisting of: oxygen, saline, and nutrients.

4. The method according to claim 1, wherein the step of measuring an amount of said substance exiting said second side is performed in a continuous manner, wherein said method yields time-dependent data.

5. The method according to claim 1, wherein said substance is selected from the group consisting of environmental contaminant, gasoline, insecticide, industrial chemicals, chemical warfare agents, creams, ointments, sprays, proteins, peptides, DNA fragments, cosmetics, solvents, carbonless copy paper.

6. The method according to claim 1, wherein the step of measuring an amount of said substance exiting the second side of said barrier comprises measuring an amount of additional substances exiting the second side of said barrier selected from the group consisting of: breakdown product, metabolites, complexes, and transformants.

7. The method according to claim 1, wherein said method provides at least one transport characteristic selected from the group consisting of a permeation rate, a breakthrough time, a normalized breakthrough time, rate of absorption, time to steady state, peak concentration at steady state, rate of elimination, and duration of action.

8. The method according to claim 1, wherein the step of exposing the first side of the barrier to said substance involves adding at least one additional substance with the substance prior to exposing the first side of the barrier.

9. The method according to claim 1, further comprising the step of chemically modifying said substance and exposing the first side of the barrier to the chemically modified substance; measuring an amount of the chemically modified substance exiting the second side of said barrier; and comparing the measured amount of said substance exiting the second side of said barrier with the measured amount of the chemically modified substance exiting the second side of said barrier in order to analyze the affect of such chemical modification on the transport properties of the substance.

10. The method according to claim 1, wherein said step of measuring the amount of said substance exiting the second side of the barrier comprises measuring the amount of said substance exiting the second side of the barrier as a function of time.

11. The method according to claim 1, wherein a second substance is applied to the first side of said barrier prior to the step of exposing the first side of the barrier to the substance.

12. The method according to claim 11, wherein said second substance is selected from the group consisting of: cosmetic, insect repellent, lotion, and cream.

13. A device for studying a transport characteristic of a substance through a barrier, comprising
   a means for exposing a first side of a barrier to a substance; and
   a means for measuring an amount of said substance exiting a second side of said barrier,
      wherein said barrier is positioned in a MIMS probe, wherein the means for exposing the first side of the barrier to the substance is adapted for placing said substance in a sample chamber of the MIMS probe, and wherein said MIMS probe is positioned in a mass spectrometer such that measuring the amount of said substance exiting the second side of said barrier is accomplished when said substance exiting the second side of said barrier is detected by the mass spectrometer.

14. The device according to claim 13, wherein said barrier is selected from the group consisting of: human skin, animal skin, fabric, latex glove material, protective clothing, artificial skin, synthetic skin, and rubber.

15. The device according to claim 14, wherein said barrier is selected from the group consisting of: human skin, animal skin, synthetic skin, and artificial skin, wherein said device is adapted to bath said barrier in a fluid comprising one or more of the group consisting of: oxygen, saline, and nutrients.

16. The device according to claim 13, wherein the means for measuring an amount of said substance exiting said second side performs said measuring in a continuous manner, said device yields time-dependent data.

17. The device according to claim 13, wherein said substance is selected from the group consisting of environmental contaminant, gasoline, insecticide, industrial chemicals, chemical warfare agents, creams, ointments, sprays, proteins, peptides, DNA fragments, cosmetics, solvents, carbonless copy paper, pesticides, toxins, polyaromatic hydrocarbons, and polychlorinated biphenyls.

18. The device according to claim 13, wherein the means for measuring n amount of said substance exiting the second side of said barrier is adapted for measuring an amount of additional substances exiting the second side of said barrier selected from the group consisting of: breakdown products, metabolites, complexes, and transformants.

19. The device according to claim 13, wherein said device provides at least one transport characteristic selected from the group consisting of a permeation rate, a breakthrough time, a normalized breakthrough time, rate of absorption, time to steady state, peak concentration at steady state, rate of elimination, and duration of action.

20. The device according to claim 2, wherein the means for exposing the first side of the barrier to said substance is adapted for adding at least one additional substance with the substance prior to exposing the first side of the barrier.

21. The device according to claim 3, wherein said means for measuring the amount of said substance exiting the second side of the barrier measures the amount of said substance exiting the second side of the barrier as a function of time.

* * * * *

UNITED STATES PATENT AND TRADEMARK OFFICE
CERTIFICATE OF CORRECTION

PATENT NO. : 6,360,588 B1 Page 1 of 1
DATED : March 26, 2002
INVENTOR(S) : Edward A. Ross, Ian R. Tebbett, Charles J. Schmidt, Timothy P. Griffin and Margaret W. Couch It is certified that error appears in the above-identified patent and that said Letters Patent is hereby corrected as shown below:

<u>Column 10,</u>
Line 24, "n amount" should read -- an amount --.
Line 34, "claim 2" should read -- claim 13 --.
Line 38, "claim 3" should read -- claim 13 --.

Signed and Sealed this

Third Day of December, 2002

JAMES E. ROGAN
*Director of the United States Patent and Trademark Office*